(12) United States Patent
Beckman et al.

(10) Patent No.: US 6,596,884 B2
(45) Date of Patent: Jul. 22, 2003

(54) SYNTHESIS OF HYDROGEN PEROXIDE

(75) Inventors: Eric J. Beckman, Pittsburgh, PA (US); Dan Hâncu, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/998,486

(22) Filed: Nov. 30, 2001

(65) Prior Publication Data

US 2002/0110516 A1 Aug. 15, 2002

Related U.S. Application Data

(62) Division of application No. 09/106,480, filed on Jun. 29, 1998.

(51) Int. Cl.⁷ .......................... C07C 45/27; C07C 50/18; C07C 15/02; C09B 1/16
(52) U.S. Cl. ...................... 552/208; 552/209; 552/236; 552/237; 552/238; 552/272
(58) Field of Search ................. 552/208, 209, 552/236, 237, 238, 272

(56) References Cited

U.S. PATENT DOCUMENTS

| | | | | |
|---|---|---|---|---|
| 2,537,975 A | * | 1/1951 | Dickey | 260/380 |
| 2,539,406 A | * | 1/1951 | Dickey | 260/380 |
| 2,624,746 A | * | 1/1953 | Dickey | 260/380 |

* cited by examiner

Primary Examiner—Samuel Barts
Assistant Examiner—Sikarl A. Witherspoon
(74) Attorney, Agent, or Firm—Bartony & Hare, LLP

(57) ABSTRACT

A method for synthesizing hydrogen peroxide comprises the steps of: synthesizing an analog of anthraquinone that is miscible or soluble in carbon dioxide; reacting the analog of anthraquinone with hydrogen in carbon dioxide to produce a corresponding analog of tetrahydroquinone; and reacting the analog of tetrahydroquinone with oxygen to produce the hydrogen peroxide and regenerate the analog of anthraquinone. A chemical compound having the formula:

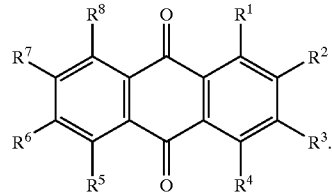

wherein $R^1$, $R^2$, $R^3$, $R^4$, $R^5$, $R^6$, $R^7$, and $R^8$ are independently, the same or different, H, $R^C$, or $R^S R^C$, wherein $R^S$ is a spacer group and $R^C$ is a fluoroalkyl group, a fluoroether group, a silicone group, an alkylene oxide group, a fluorinated acrylate group, or a phosphazine group, and wherein at least one of $R^1$, $R^2$, $R^3$, $R^4$, $R^5$, $R^6$, $R^7$, and $R^8$ is not H.

13 Claims, 8 Drawing Sheets

Idealized asymmetric cloud point curve

Figure 1

Effect of tail length on phase behavior of 2-AQ-NHCO-Kr:
(■) 2-AQ-NHCO-2500; (▲) 2-AQ-NHCO-5000
(●) 2-AQ-NHCO-7500

*Figure 2*

Effect of tail length on phase behavior of 2-AQ-CH$_2$-OCO-Kr:
(▲) 2-AQ-CH$_2$-OCO-700; (●) 2-AQ-CH$_2$-OCO-2500
(▼) 2-AQ-CH$_2$-OCO-5000; (■) 2-AQ-CH$_2$-OCO-7500

*Figure 3*

Effect of head group on phase behavior:
(▲) 2-AQ-CH₂-OCO-5000; (▼) 2-AQ-N(Me)CO-5000
(●) 1-AQ-NHCO-5000; (■) 2-AQ-NHCO-5000

Figure 4

Effect of topology on phase behavior of Twin (2500)-AQ:
(▼) 1,4-Twin (2500)-AQ; (▲) 1,2-Twin (2500)-AQ;
(●) 2,6-Twin (2500)-AQ;

*Figure 5*

Hydrogenation of 10 mM 2-AQ-NHCO-5000 in liquid $CO_2$ (P=3450 Psi, T=25 C) in the presence of powdered Pd (1%) / $Al_2O_3$ catalyst (3.14g/l) monitored by UV spectroscopy

Figure 6

Calculated diffusion coefficients for 2-AQ-NHCO-Kr and 2-AQ-CH$_2$-OCO-Kr IN LIQUID CO$_2$ AT P=3450 Psi and T=25 C

Figure 7

Figure 8
EXPERIMENTAL SETUP

SYNTHESIS OF HYDROGEN PEROXIDE

CROSS-REFERENCE TO RELATED APPLICATIONS

This application is a divisional application of U.S. patent application Ser. No. 09/106,480, filed on Jun. 29, 1998, the contents of which is hereby incorporated by reference.

GOVERNMENT INTERESTS

This invention was made with government support under grant number CTS-9523993 awarded by the National Science Foundation. The government has certain rights in this invention.

FIELD OF THE INVENTION

The present invention relates to the synthesis of hydrogen peroxide, and more particularly, to the synthesis of hydrogen peroxide without the use of an organic solvent.

BACKGROUND OF THE INVENTION

Hydrogen peroxide ($H_2O_2$) is often considered to be a "green" material, in that it is increasingly used to replace chlorine-containing reagents in paper bleaching and in water purification. For this reason, as well as others, hydrogen peroxide production is estimated to increase steadily through the beginning of the next century.

The production of hydrogen peroxide is a mature process in that the general procedure has not changed appreciably in twenty years. Indeed, recent research publications in the area of hydrogen peroxide synthesis are somewhat scarce. Typically, hydrogen peroxide is generated in a two-step process, wherein hydrogen is first reacted with a 2-alkyl anthraquinone (usually 2-ethyl or 2-amyl anthraquinone) in an organic solvent to produce the corresponding tetrahydroquinone (2-alkyl tetrahydroquinone). The reaction is catalyzed by a simple palladium-on-alumina catalyst. Conditions for this reaction are typically 30 to 70° C. with hydrogen pressures up to 300 psi. Given the nature of the reactants, the reactor contains three phases (gas, liquid, and solid catalyst) and previous work has shown that the reaction is completely mass transfer limited, such that the rate of the reaction is essentially the rate at which hydrogen diffuses into the liquid phase. Partly as a result of this inefficiency of hydrogen use, side reactions (hydrogenation of one or both of the aromatic rings) also occur, and byproducts build up during repeated cycling of the anthraquinone. These byproducts must periodically be removed and treated. The organic solvent employed is typically a mixture of an aromatic (a good solvent for the anthraquinone) and a long-chain alcohol (a good solvent for the hydroquinone).

The second step of the process involves oxidation of the hydroquinone, regenerating the anthraquinone and producing hydrogen peroxide. Here the catalyst is retained in the first reactor, and the solution of alkyl anthraquinone, alkyl tetrahydroquinone and organic solvent (the working solution) is transferred to the second reactor, where the hydroquinone is reacted with oxygen (as air or oxygen). This reaction is uncatalyzed. Similar to the first reaction, the second reaction is mass transfer limited by the rate at which oxygen can diffuse from the gas to liquid phases. Finally, the hydrogen peroxide is stripped from the organic solvent via liquid-liquid extraction with water and sold as an aqueous mixture (usually 30 to 50%).

Because the final step in the production of hydrogen peroxide involves a liquid-liquid extraction between aqueous and organic phases, the final product is contaminated to some extent by the organic phase. Given that $H_2O_2$ is promoted as a green reagent for paper production, and is also used in water purification, the organics in the final product must be minimized. Significant effort is thus made to strip the organic contaminants from the product.

It is, therefore, very desirable to develop reactants and processes for the synthesis of hydrogen peroxide that minimize or eliminate the use of organic solvents.

SUMMARY OF THE INVENTION

In general, the present invention provides a method for synthesizing hydrogen peroxide, comprising the steps of:

synthesizing an analog of anthraquinone that is miscible with (in the case of a liquid analog) or soluble in (in the case of a solid analog) carbon dioxide;

reacting the analog of anthraquinone with hydrogen in carbon dioxide to produce a corresponding analog of tetrahydroquinone; and reacting the analog of tetrahydroquinone with oxygen to produce the hydrogen peroxide and regenerate the analog of anthraquinone.

Preferably, the regenerated analog of anthraquinone is recycled for future use.

The step of synthesizing an analog of anthraquinone that is miscible in carbon dioxide preferably comprises the step of attaching to anthraquinone at least one modifying or functional group that is relatively highly soluble in $CO_2$ ("$CO_2$-philic"). The miscibility/solubility of the resulting analogs of anthraquinone are several orders of magnitude greater at the operating pressures of the present invention than the solubility of 2-alkyl anthraquinone in carbon dioxide at pressures equal to or below 5000 psi. Alkylanthraquinones used in the commercial synthesis of hydrogen peroxide do not exhibit appreciable solubility in carbon dioxide at pressures below 5000 psi. In that regard, a number of studies have explored the solubility of alkyl-functional anthraquinones in carbon dioxide and found generally that the system exhibits solid-fluid phase behavior with maximum solubilities of approximately $10^{-2}$ mM. See, for example, Joung, S. N., Yoo, K. P., *J. Chem. Eng. Data*, 43, 9 (1998). Coutsikos, P., Magoulos, K., Tassios, D., *J. Chem. Eng. Data*, 42, 463 (1997). Swidersky, P., Tuma, D., Schneider, G. M., J., *Supercrit. Fl.*, 9, 12 (1996). *ibid*, 8, 100 (1995).

A liquid-liquid phase envelope is preferably formed in the functionalized anthraquinone-carbon dioxide systems of the present invention at relatively moderate pressures. The operating pressure at which the analogs of anthraquinone (and preferably the analogs of hydroquinone) are reacted in carbon dioxide is preferably no greater than approximately 5000 psi. More preferably, the operating pressure is no greater than approximately 3000 psi. Even more preferably, the operating pressure is no greater than approximately 2500 psi. Most preferably, the operating pressure is no greater than approximately 1500 psi. The operating pressure at which the analogs of anthraquinone are reacted with hydrogen (and, preferably, the operating pressure at which the analogs of hydroquinone are reacted with oxygen) is preferably chosen such that it is above the cloud point curve (and, preferably, above the maximum of the cloud point curve) in the liquid-liquid phase envelop (or liquid-fluid phase envelope when operating at supercritical conditions). In the region above the cloud point curve, single-phase behavior is observed.

The operating temperature of the present reactions is preferably between approximately 0° C. and approximately 100° C. The operating temperature of the present reactions is more preferably between approximately 20° C. and approximately 40° C. Most preferably, the operating temperature of the present reactions is approximately 25° C. (room temperature).

Preferably, the $CO_2$-philic functionalized anthraquinones and the corresponding hydroquinones of the present invention exhibit reactivity similar to the 2-alkyl anthraquinone and hydraquinones used in the current commercial synthesis of hydrogen peroxide. Indeed, the kinetic rate constants calculated for the oxygenation of the functionalized anthraquinones of the present invention were found to be approximately ten time greater than anthraqinone. The use of $CO_2$-philic groups to increase the solubility of a molecule in carbon dioxide is also discussed in U.S. Pat. No. 5,641,887, the disclosure of which is incorporated herein by reference.

In general, the analog of anthraquinone preferably has the formula:

At least one of $R^1$, $R^2$, $R^3$, $R^4$, $R^5$, $R^6$, $R^7$, and $R^8$ (corresponding to the 1, 2, 3, 4, 5, 6, 7, and 8 carbons on the anthraquinone ring structure) is a modifying group or functional group that is miscible/souble in carbon dioxide. Attachment of one or more such $CO_2$-philic groups to anthraquinone results in an analog of anthraquinone that is miscible/soluble in carbon dioxide. In that regard, $R^1$, $R^2$, $R^3$, $R^4$, $R^5$, $R^6$, $R^7$, and $R^8$ are preferably, independently, the same or different, H, $R^C$ or $R^S R^C$, wherein $R^S$ is a connector or a spacer group and $R^C$ is a fluoroalkyl (fluorinated alkyl) group, a fluoroether (fluorinated ether) group, a silicone group, an alkylene oxide group, a phosphazene group or a fluorinated acrylate group. At least one of $R^1$, $R^2$, $R^3$, $R^4$, $R^5$, $R^6$, $R^7$, and $R^8$ is not H. Preferably, $R^C$ is a fluoroalkyl group, a fluoroether group or an alkylene oxide group. More preferably, $R^C$ is a fluoroether group or an alkylene oxide group.

The spacer group, $R^S$, when present, can simply be a connective group used to attach a $CO_2$-philic group to anthraquinone or can additionally act to space the $CO_2$-philic group away from the anthraquinone. The spacer group is preferably a group which provides a simple synthetic route to achieve the desired analog of anthraquinone without substantially adversely affecting the miscibility of the analog of anthraquinone in carbon dioxide or the reactivity of the analog of anthraquinone and the corresponding hydraquinone in the synthesis of hydrogen peroxide. For example, the spacer group can be an alkylene group, an amino group, an amido group, an ester group or an alkyl ester group. As used herein in connection with $R^S$, the term "alkylene group" refers to a linear or branched alkylene group. A linear alkylene group, for example, has the formula —$(CH_2)_n$—. As used herein in connection with $R^S$, the term "amino group" refers to a secondary amino group having the formula —NH— or a tertiary amino group having the formula —$NR^{11}$H—, wherein $R^{11}$ can generally be any substituent that doesn't interfere with the reactivity of the desired analog. For example, $R^{11}$ can be an alkyl group. As used herein in connection with $R^S$, the term "amido group" refers to secondary amido having the formula —NHCO—, or a tertiary amido group having the formula —$NR^{11}$CO— wherein $R^{11}$ is as defined above. As used herein in connection with $R^S$, the term "ester group" refers to a group having the formula —OCO—. As used herein in connection with $R^S$, the term "alkyl ester group" refers to a group having the formula —$R^{12}$OCO—, wherein $R^{12}$ is an alkyl group. The spacer group itself need not be $CO_2$-philic. If it is desired to use the spacer group to space the $CO_2$-philic group away from the anthraquinone ring structure, an alkalene group is preferably used, either alone or in combination with another connective group.

The total molecular weight of the $CO_2$-philic groups $R^C$ attached to the analog of anthraquinone is preferably between approximately 200 and approximately 7500 to make the analog of anthraquinone miscible/soluble in carbon dioxide. One or more $CO_2$-philic groups can be attached to the anthraquinone ring structure. For example, each of $R^2$, $R^3$, $R^6$, and $R^7$, can comprise a perfluoroalkyl group having a molecular weight of 50. More preferably, the total molecular weight of the $CO_2$-philic groups is between approximately 500 and approximately 5000. Most preferably, the total molecular weight of the $CO_2$-philic groups is between approximately 500 and approximately 1500.

The fluoroalkyl groups of the present invention are preferably linear perfluoroalkyl groups having the formula/repeat group:

wherein g is an integer.

The fluoroether groups of the present invention are preferably perfluorinated and have the formula/repeat group:

wherein each of x, y and z is an integer greater than or equal to 0 and at least one of x, y and z is not equal to 0.

The silicone groups of the present invention preferably have the formula/repeat group(s):

wherein $R^9$ and $R^{10}$ are chosen to not substantially affect the $CO_2$-philic nature of the silicone group or the reactivity of the functionalized analogs of anthraquinone. $R^9$ and $R^{10}$ may, for example, be, independently, the same or different, H, an alkyl group, an aryl group, an alkenyl group, or an alkoxyl group, and wherein b is an integer. Preferably, $R^9$ and/or $R^{10}$ is a fluoroalkyl group.

The alkylene oxide groups of the present invention preferably have the formula/repeat group:

wherein d is an integer and e is an integer.

The fluorinated acrylate groups of the present invention preferably have the formula/repeat group:

wherein g and j are integers.

The phosphazine groups of the present invention preferably have the formula/repeat group:

wherein m is an integer and $R^9$ and $R^{10}$ are as defined above.

The oxidation of the hydroquinone of the present invention preferably takes place in carbon dioxide at substantially the same pressure as the hydrogenation reaction. The hydrogen peroxide product of the present invention is preferably recovered via a liquid-liquid extraction between the carbon dioxide phase and an aqueous phase. The liquid-liquid extraction is preferably conducted without significantly reducing the operating pressure. Likewise, the carbon dioxide is preferably recycled to the extractor without a significant drop in pressure. Such a process for separation/recovery of hydrogen peroxide product avoids the high costs associated with recompression, while taking full advantage of carbon dioxide's green properties in running a contamination-free liquid-liquid extraction between a carbon dioxide phase and an aqueous phase.

Moreover, using carbon dioxide as the solvent for the process of the present invention allows one to generate a single phase system of hydrogen plus anthraquinone (for the first reaction of the synthesis), or oxygen plus tetrahydroanthraquinone or tetrahydroquinone (for the second reaction of the synthesis). It is known that hydrogen is completely miscible with carbon dioxide above a temperature of approximately 31° C. Hydrogen and carbon dioxide have been found to not form separate phases under the operating conditions of the present invention. The reactions can thus be carried out without the mass transfer limitation of the current commercial process for the synthesis of hydrogen peroxide, suggesting that one could operate more efficiently, using less hydrogen and/or at lower temperatures, while producing fewer byproducts.

Furthermore, the operating pH for the stripping operation to recover the hydrogen peroxide from the organic phase into the aqueous stream in the current commercial process for the synthesis of hydrogen peroxide is preferably approximately 3.0 to partition the hydrogen peroxide into the aqueous phase. Because the carbon dioxide of the present invention dissolves in water to form carbonic acid, the pH of the water in the presence of high pressure carbon dioxide is approximately 3.0, assisting in partitioning the hydrogen peroxide into the aqueous phase.

The present invention also provides a chemical compound having the formula:

wherein $R^1$, $R^2$, $R^3$, $R^4$, $R^5$, $R^6$, $R^7$, and $R^8$ are as described above.

Further, the present invention provides a chemical compound having the formula:

wherein $R^1$, $R^2$, $R^3$, $R^4$, $R^5$, $R^6$, $R^7$, and $R^8$ are as described above.

Still further, the present invention provides method for synthesizing hydrogen peroxide, comprising the steps of:
synthesizing an analog of anthraquinone having the formula:

wherein $R^1$, $R^2$, $R^3$, $R^4$, $R^5$, $R^6$, $R^7$, and $R^8$ are as described above;
reacting the analog of anthraquinone with hydrogen to produce a corresponding tetrahydroquinone having the formula;

reacting the tetrahydroquinone with oxygen to produce the hydrogen peroxide and regenerate the analog of anthraquinone.

It has been found experimentally that analogs of anthraquinone functionalized with the $CO_2$-philic functional groups of the present invention are typically liquids at relatively low temperatures and pressures. For example, anthraquinones functionalized with fluoroether groups of the present invention are typically liquid at room temperature and one atmosphere pressure. Unlike the current commercial process using 2-alkyl anthraquinone (a solid), one can generate hydrogen peroxide from the liquid functionalized analogs of anthraquinones of the present invention without the use of any solvent (including carbon dioxide). In such a process, the liquid analog of anthraquinone is reacted with hydrogen in the first reaction to produce the corresponding hydroquinone. The corresponding hydroquinone is then oxidated as described above to produce hydrogen peroxide. The hydrogen peroxide product is preferably recovered via liquid-liquid extraction with an aqueous phase. The $CO_2$-philic groups of the present invention generally reduce the solubility of the analogs of anthraquinone in water, typically rendering the anthraquinone very hydrophobic and greatly reducing contamination of the aqueous phase therewith (as compared to the current commercial process) during extraction of the hydrogen peroxide product. Synthesizing hydrogen peroxide with a liquid analog of anthraquinone and without solvent reduces equipment costs as compared to synthesis in carbon dioxide, but, unlike the process in carbon dioxide, the oxidation and hydrogenation reaction would be mass-transfer limited.

DETAILED DESCRIPTION OF THE INVENTION

Carbon dioxide has received significant scientific interest over the past 15 years because it is considered a "green" alternative to conventional organic solvents. Carbon dioxide is inexpensive (approximately $80/ton, 1–2 orders of magnitude less than conventional solvents), non-flammable, not currently regulated as a volatile organic chemical by the US EPA, and not regulated by the U.S. FDA in food or pharmaceutical applications. The latter advantage has lead to the commercialization of several large (greater than 50 million pounds per year) food processing ventures using carbon dioxide.

Carbon dioxide's inherent "green" properties make it particularly desirable for use in liquid-liquid extraction from water. While any organic solvent will contaminate water to a certain degree in a liquid-liquid extraction, in the case carbon dioxide this "contamination" obviously does not require remediation. Moreover, use of carbon dioxide as a solvent in conjunction with gaseous reactants can eliminate certain transport limitations to reaction.

Although carbon dioxide possesses distinct advantages as a solvent, it also exhibits a number of disadvantages which have limited commercial applications, for the most part, to food processing and polymer foam production. First, use of carbon dioxide (in either the liquid or supercritical state) requires the use of elevated pressures (the vapor pressure of carbon dioxide at room temperature is over 900 psi). Consequently, design and construction of equipment is significantly more expensive than for analogous processes carried out at atmospheric pressure.

Second, utility costs resulting from processing with high pressure carbon dioxide can be prohibitively high. For example, while it has been suggested that depressurization of a carbon dioxide solution to one atmosphere is an easy route to recovery of products, a carbon dioxide-based process may not be economically viable if extensive depressurization is used to recover dissolved products. Indeed, the known carbon dioxide-based coffee decaffeination process is economically viable, in part, because the carbon dioxide is not depressurized to recover the caffeine following stripping of caffeine from the coffee beans. That process uses water to extract the caffeine from the carbon dioxide in a countercurrent liquid-liquid column (the caffeine is ultimately recovered via reverse osmosis).

Another significant obstacle to the use of carbon dioxide as a solvent in conventional chemical processes is its low solvent power. Although carbon dioxide's solvent power was once suggested to be comparable to that of liquid alkanes, recent research has shown that this generalization is in error. Calculated solubility parameters for carbon dioxide are approximately 4–5 cal/cm$^3$ in the liquid state, similar to that of fluorinated materials and slightly lower than that for silicones. It is generally accepted that carbon dioxide will not solubilize significant quantities of polar, high molecular weight, or ionic compounds. Low solubilities of compounds of interest require large volumes of carbon dioxide in a potential process, and thus the chance for favorable economics diminishes.

Synthesis of $CO_2$-Miscible Functionalized Anthraquinones (FAQ'S)

In the present invention, novel, highly $CO_2$-miscible/soluble analogs of 2-alkyl anthraquinones are first synthesized. These functionalized analogs are then use in the synthesis of hydrogen peroxide in carbon dioxide via sequential reaction with hydrogen, and then oxygen as illustrated below.

-continued

H₂FAQ

FAQ 2-alkyl anthraquinones typically used in the commercial synthesis of hydrogen peroxide exhibit negligible solubility in carbon dioxide at pressures up to 5000 psi at room temperature. It has been discovered that highly $CO_2$-soluble/miscible analogs of anthraquinone can be synthesized via modification or functionalization of anthraquinone with $CO_2$-philic groups. Such functionalized anthraquinone are often abbreviated as FAQ's herein. The $CO_2$-philic groups suitable for use in the present invention include, for example, fluoroether groups, fluoroalkyl groups, silicones, fluorinated acrylates and phosphazines.

Analogs of 2-alkyl anthraquinone have been synthesized via the reaction of a commercially available anthraquinone functionalized with a first reactive group with a $CO_2$-philic group functionalized with a second reactive group, wherein the first reactive group and the second reactive group are selected to react to link the $CO_2$-philic group to the anthraquinone ring structure via a resultant connector or spacer group $R^S$. The $CO_2$-philic group can also be directly linked to the anthraquinone ring structure. oligomeric (generally, with a molecular weight above 50) fluoroether $CO_2$-philic groups were used as models in the present studies. For example, fluoroether acid chloride (generated from a 2500 molecular weight (MW) fluoroether carboxylic acid obtained from DuPont) was reacted with 2-amino anthraquinone (obtained from Aldrich Chemical). In that reaction, the acid chloride functional group and the amino functional group react to form an amide connector or linkage.

The functionalized fluoroether anthraquinone analogs of the present studies are much more soluble in carbon dioxide than a 2-alkyl anthraquinone. Moreover, the $CO_2$-miscible/soluble analogs of anthraquinone of the present invention were found to retain their reactivity towards hydrogen.

Phase Behavior of Functionalized Anthraquinones

Figure 1:
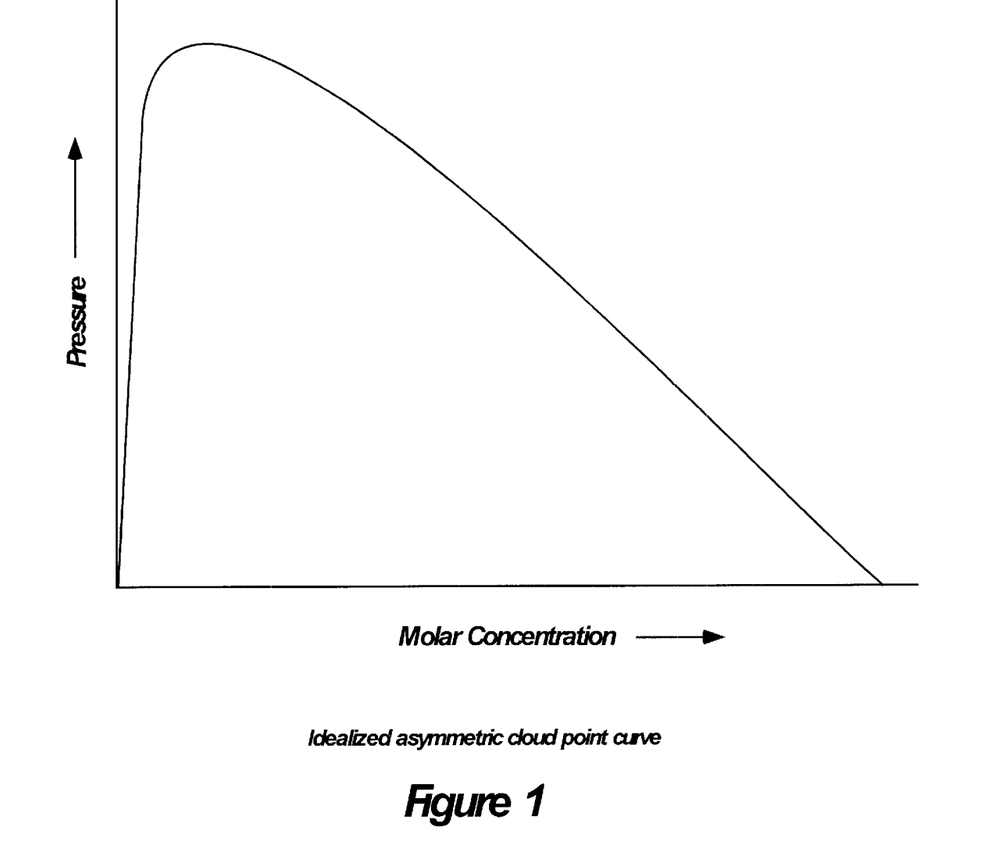
FIG. 1 illustrates an asymmetric cloud point curve for a functionalized anthraquinone-carbon dioxide system.

Mixtures of the FAQ analogs of the present invention and carbon dioxide were found to exhibit asymmetric liquid-liquid phase envelopes in P-x space. An idealized representation of such an asymmetric liquid-liquid phase envelope is illustrated in FIG. 1. To achieve complete miscibility over a broad range of concentrations, the operating pressure is preferably chosen to be above the maximum of the cloud point curve. However, the reactions of the present invention are preferably operated at room temperature and at as low a pressure as possible to reduce operating costs. Phase behavior studies of a number of fluoroether model FAQ's of the present invention were thus undertaken to study the effect of various parameters on the miscibility of the FAQ analogs in carbon dioxide.

In that regard, the effects of three different parameters on solubility of the FAQ analogs in carbon dioxide have been studied: (1) the effect of tail length, (2) the effect of head group, (3) the effect of numbers of tails and the position of the tail on the anthraquinone aromatic rings.

Figure 2:
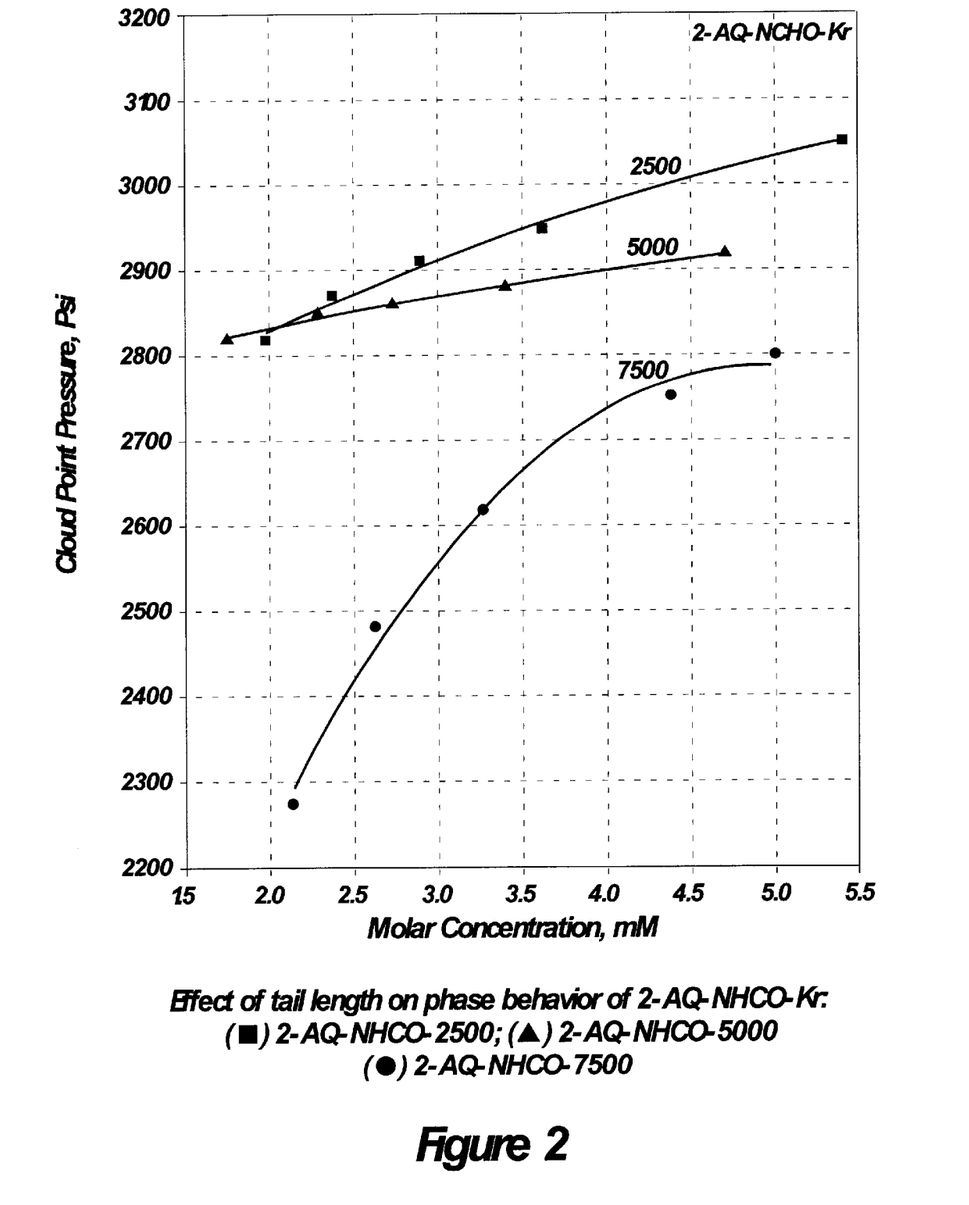
FIG. 2 illustrates the effect of functional group length upon the phase behavior of an analog of anthraquinone.
Figure 3:
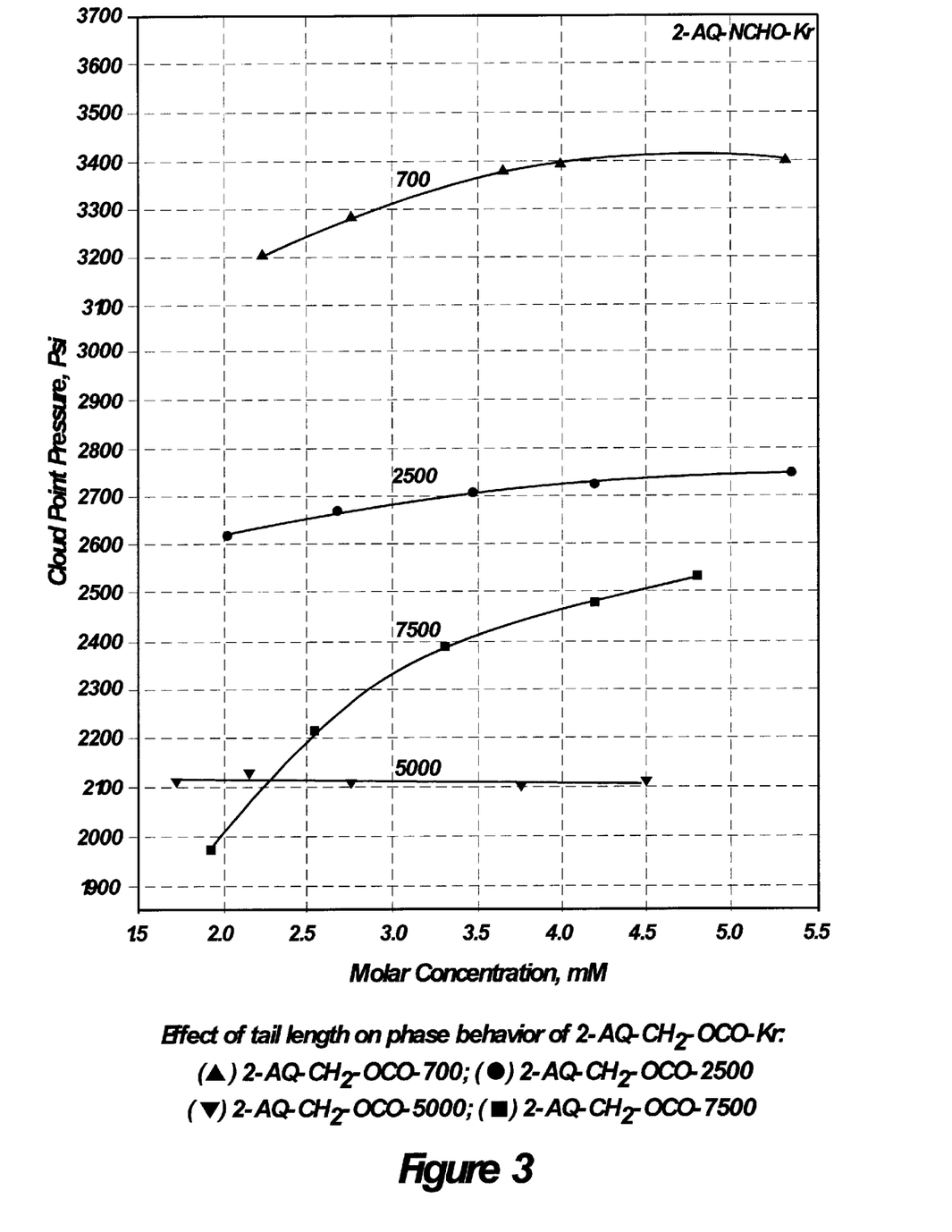
FIG. 3 illustrates the effect of functional group length upon the phase behavior of another analog of anthraquinone.

FIGS. 2 and 3 depict a portion of the cloud point curves of a number of FAQ's having different tail lengths. In FIG. 2, the effect of tail length (MW=2500, 5000 and 7500) upon the miscibility in carbon dioxide of a fluoroether oligomer attached to the 2-carbon of the anthraquinone ring by an amide connector group is illustrated. In FIG. 3, the effect of tail length (MW=700, 2500, 5000 and 7500) upon the miscibility in carbon dioxide of a fluoroether oligomer attached to the 2-carbon of the anthraquinone ring by an ester connector group is illustrated. As illustrated in FIGS. 2 and 3, the pressure required to achieve miscibility generally reduces with increasing tail length. However, as illustrated in a comparison of the cloud point curves of the 5000 and 7500 MW analogs in FIG. 3, as tail length (MW) increases, the gain in solubility due to a higher contribution of the hydrophobic/$CO_2$-philic group ($R^C$) is eventually overcome by the larger value of the entropy of mixing. At this point, the global effect of these two factors is a decrease in solubility compared to lower molecular weigh tails.

Figure 4:
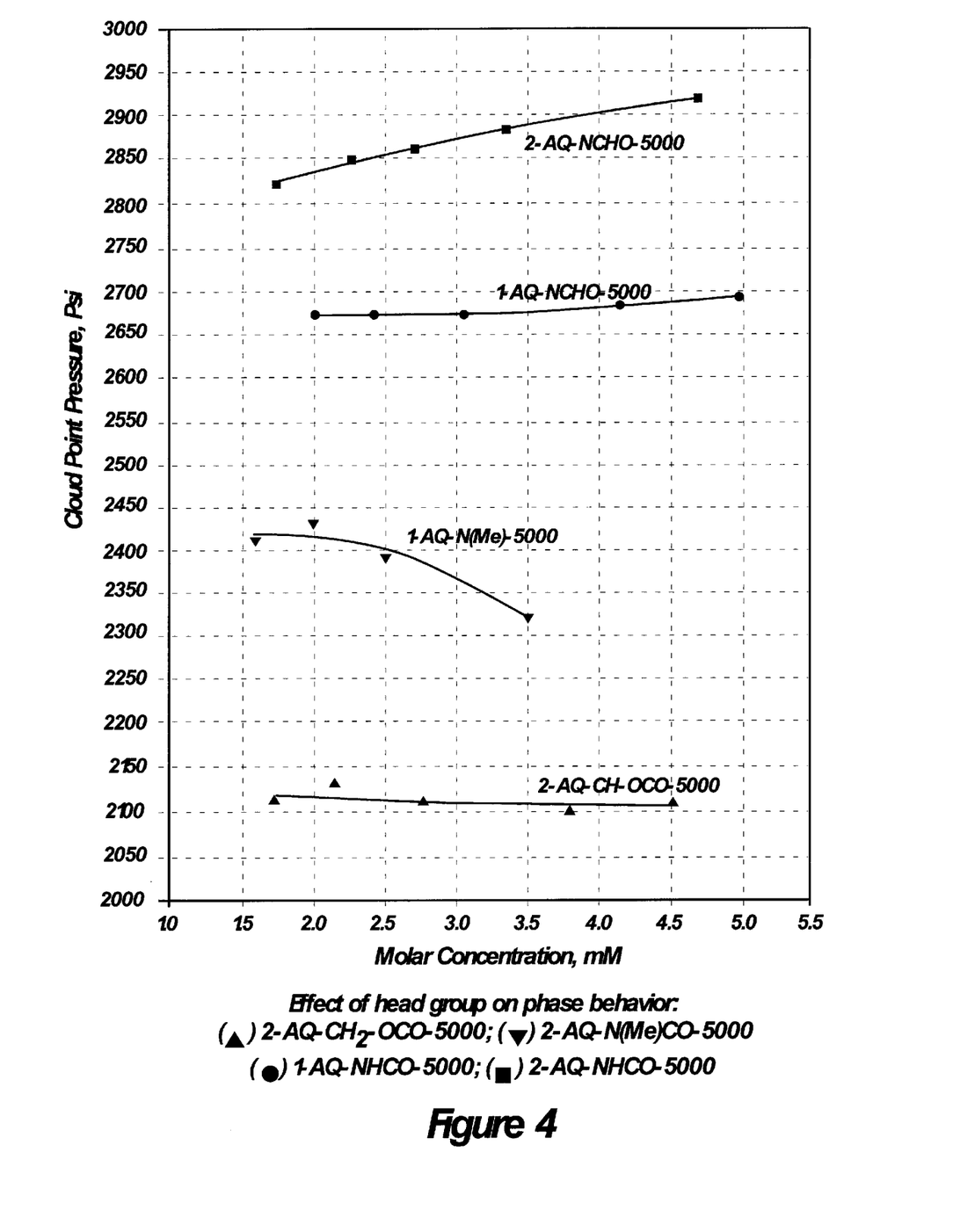
FIG. 4 illustrates the effect of the identity of a spacer group and the position of the functional group upon the phase behavior of an analog of anthraquinone.

In the studies of FIG. 4, the effect of the identity of the connector or spacer group ($R^S$) and the position thereof upon the miscibility of the FAQ is illustrated. As illustrated, the miscibility of the FAQ with the ester spacer group is greater than those with the amide linkage. This phenomenon is believed to result from the ability of certain spacer groups to hydrogen bond, and thus resist salvation by carbon dioxide. Such hydrogen bonding does not occur in the case of the methyl ester spacer group (shown below) of FIG. 4.

No Hydrogen Bonding

Likewise, hydrogen bonding does not occur in the case of a tertiary amide spacer groups such as an —NCH₂CO— (shown below).

No Hydrogen Bonding

In general, replacement of the secondary amide proton with a methyl group is found to drop the cloud point curve by approximately 700 psi. Replacement of the tertiary amide spacer with an ester spacer drops the cloud point curve approximately an additional 200 psi, revealing a thermodynamic preference of carbon dioxide for the 2-methyl ester linkage over the N-substituted amide.

Figure 5:
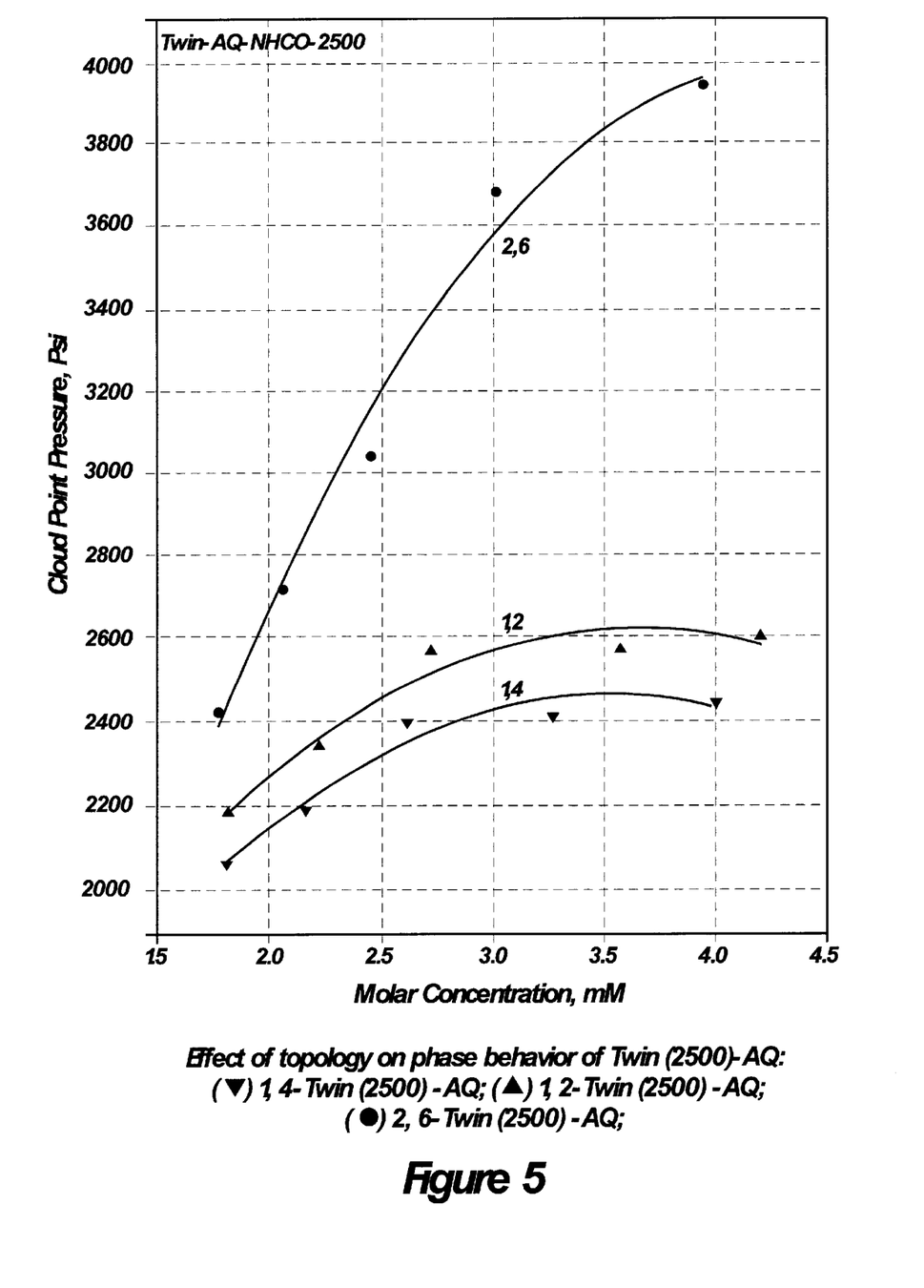
FIG. 5 illustrates the effect of the position of the functional groups upon the phase behavior of a difunctionalized analog of anthraquinone.

Furthermore, the position of spacer groups capable of forming hydrogen bonds also affects the miscibility of the FAQ. As illustrated in FIGS. 4 and 5 and in the chemical formulas below, 1-, 1,4- and 1,2-substitutions, which can readily form intramolecular hydrogen bonds, exhibit greater miscibility than 2-, and 2,6-substitutions, which can only form intermolecular hydrogen bonds.

Intermolecular Hydrogen Bonding

Intramolecular Hydrogen Bonding

Rate of Reaction/Diffusion Coefficients

In a heterogeneous catalytic system as occurs in the hydrogenation reaction of the present invention, the overall rate of reaction can be controlled or limited either by the inherent kinetics of the reaction or by the rate of diffusion of one or more of the reactants to the catalytic sites. The effectiveness factor, or η, is the ratio of the actual rate to that of the purely kinetic rate, such that an effectiveness factor of 1.0 indicates a purely kinetically controlled reaction, while lower values imply mass transport limitations. The effectiveness factor is a strong function of the Thiele modulus (a dimensionless number incorporating both the true kinetic rate constant and the diffusion coefficient for the reactants within the catalyst particle). As the diffusion coefficient increases, the Thiele modulus decreases and the effectiveness factor approaches 1.0.

Figure 7:
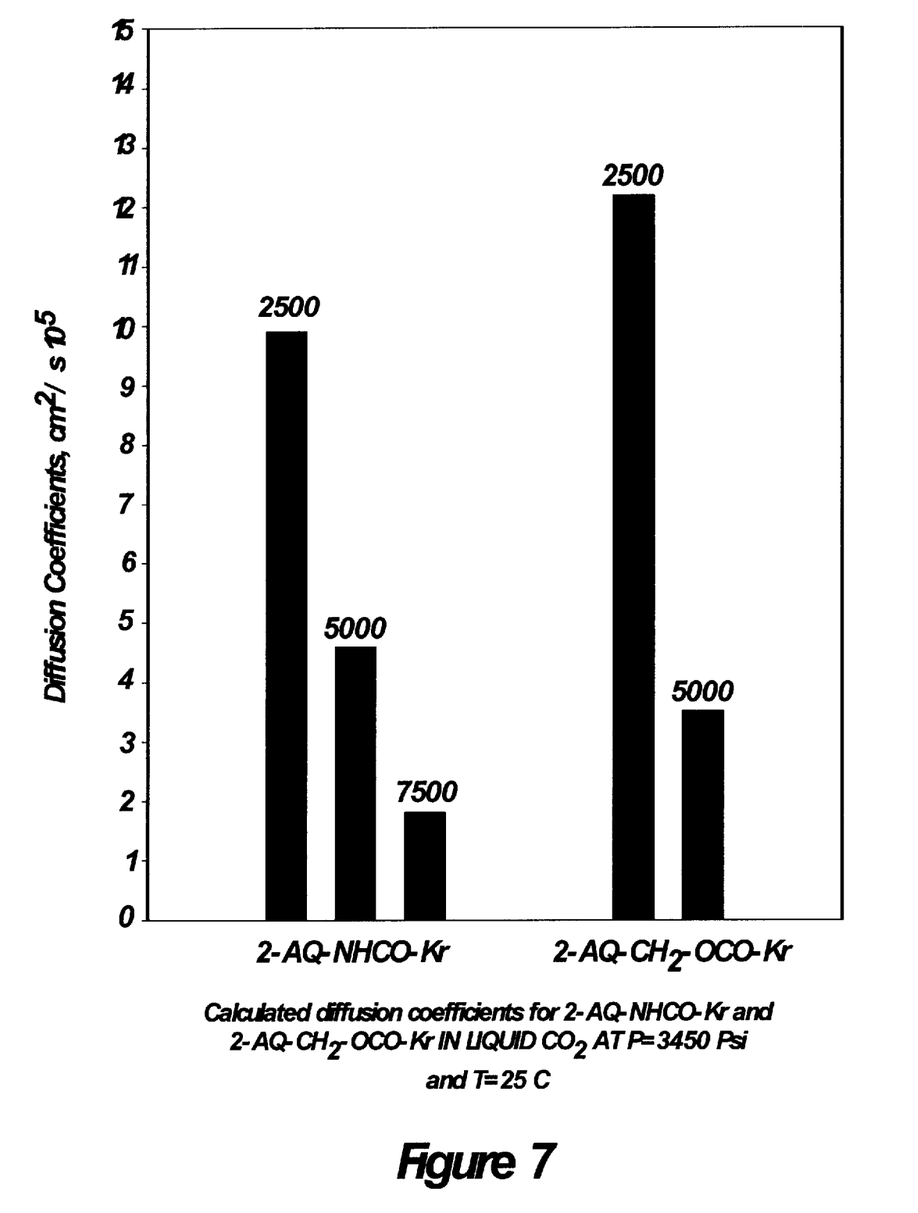
FIG. 7 illustrates the effect of the length of molecular weight of the $CO_2$-philic functional group upon the diffusion coefficient.

In the present studies, effective psuedo-first order rate constants, $k_{eff}$, (including contributions from both the true kinetic rate constant and the diffusion coefficient of the functionalized analog of anthraqiunone in the pores of the catalyst) were studied for the hydrogenation reaction. The calculated kinetic data and diffusion coefficients for functional groups of different lengths and spacer groups are set forth in Table 2 and in FIG. 7. As illustrated, the diffusion coefficient was found to decrease with increasing functional group length.

Experimental

Materials and Methods

Oligomers of hexafluoropropylene functionalized at one end with a carboxilic group (DuPont, FW=700, 2500, 5000, 7500), thyonyl chloride (99.9%, Aldrich), N, N dimethyl formamide (Aldrich), and perfluoro-2,5,8-trimethyl-3,6,9-trioxadodecanoyl fluoride (Aldrich) were used as received. 1-aminoanthraquinone(97%, Aldrich), 1-(methylamino) anthraquinone (98%, Aldrich), 2-aminoanthraquinone (technical grade), 1,2-diaminoanthraquinone (Aldrich), 1,4-diaminoanthraquinone (Aldrich, 85%), 2,6-diaminoanthraquinone (Aldrich, 97%), 2-hydroxymethyl)-anthraquinone were used as purchased. Perfluoro 1,3-dimethylcyclohexane (Aldrich, 80%) and 1,1,2-trichlorotrifluoroethane were distilled and dried on 4A molecular sieves. Palladium, 1 wt % on alumina powder (Aldrich) was used as received. Pd catalysts with larger particle sizes were prepared by compressing the powdered catalyst into pallets which were sieved into 3 fractions: $20<d_p<40$ mesh, $40<d_p<60$ mesh, , $60<d_p<80$ mesh.

Phase behavior of FAQ's was measured in a high pressure, variable volume view cell (D. B. Robinson and Associates). A known amount of FAQ was loaded on the top of a quartz cell sealed inside a steel housing. The movement of a floating piston that separates the transmitting-pressure fluid, in this case, silicone oil, from the mixture to be analyzed, regulates the pressure inside the cell. After a known amount of $CO_2$ was added to the cell by one of the two Ruska syringe pumps, the pressure was raised by injection of silicone oil to a point where a single phase existed. Phase transition was determined by slowly lowering the pressure till the outset of a phase separation, indicated by a slight turbidity, was observed. Subsequently, a new amount of $CO_2$ was injected in the cell, and the procedure was repeated for another concentration of FAQ till the phase diagram was completed. Solubility data of different FAQ's described herein is presented in FIGS. 2 through 5.

EXAMPLE 1

This example describes the procedure used to synthesize mono amide functionalized anthraquinones illustrated below (entries 1–5 in Table 1 below).

X—(Kr-CONH)—AQ;

x = 1 or 2

In the abbreviation x—(Kr—CONH)—AQ, x represents the position of the functional group (that is, either on the 1 or 2 carbon of the anthrqauinone ring structure in this example), Kr represents the fluoroether group ($R^C$), —CONH— represents the amide connecting or spacer group ($R^S$) that links the fluoroether group to the anthraquinone ring structure, and AQ represents the anthraquinone ring structure.

2 mmole of fluoroether acid chloride (MW=2500, 5000, 7500) and 4 mmole of mono-amino anthraquinone were heated at 100° C. under nitrogen atmosphere. After five hours of reaction, the reaction mixture was dissolved in 50 cm³ of perfluoro 1,3-dimethylcyclohexane, the excess of amine was removed by filtration, and the solvent was evaporated under vacuum. The product was washed several times with acetone. The chemical structure of the product was established by its NMR and IR spectrum. (entries 1–5 in Table 1).

EXAMPLE 2

This example describes the procedure used to synthesized di-amino functionalized anthraquinones illustrated below (entries 6–8 in Table 1).

x,y-Twin(2500)—AQ;
(x = 1, y = 2), (x = 1, y = 4), (x = 2, y = 6)

In the abbreviation x, y-Twin (2500)-AQ, x and y represent the position of the functional groups on the anthrqauinone ring structure, Twin(2500) represents two fluoroether groups ($R^C$), each having a molecular weight of approximately 2500, and AQ represents the anthraquinone ring structure. The —CONH— amide connecting or spacer group ($R^S$) that links each of the fluoroether groups to the anthraquinone ring structure is not set forth in the abbreviation.

2 mmole of diaminoanthraquinone and 4 mmole fluoroether acid chloride were heated at 100° C. in the presence of 4.5 mmole of pyradine under nitrogen atmosphere. After 5 hours of reaction, 50 ml of perfluoro 1,3-dimethylcyclohexane was added to the mixture, and the pyridinium chloride formed in the reaction along with the excess of pyridine was washed with a solution of 5% HCl in a separatory funnel. The solvent was evaporated under vacuum in the presence of 10 cm³ benzene which helped the removal of water emulsified during the wash with hydrochloric acid solution. The chemical structure of the product was established by its NMR and IR spectrum (entries 6–8 in Table 1).

EXAMPLE 3

The following example describes the procedure used for synthesis of fluoroether ester anthraquinones illustrated below (entries 9–12 in Table 1).

2-(Kr-COO—CH₂)—AQ

In the abbreviation x—(Kr—COO—CH₂)AQ, 2 represents the position of the functional group on the 2 carbon of the anthrqauinone ring structure in this example, Kr represents the fluoroether group ($R^C$), —COO—CH₂— represents the methyl ester spacer group ($R^S$) that links the fluoroether group to the anthraquinone ring structure, and AQ represents the anthraquinone ring structure.

3.5 moles of fluoroether acid chloride was added dropwise in a reaction mixture consisting of 0.953 g (4 mmoles) of 2-(hydroxymethyl)-anthraquinone and 0.32 ml (0.31 g, 4 mmoles) of pyridine. After the reaction mixture was mixed for 10–15 minutes at room temperature, 30 cm³ of 1,1,2-trifluorotrichloroethane was added and the mixture was refluxed for additional 3 hours. After the completion of the reaction, pyridinium chloride (white salt) formed in the reaction was removed by filtration under vacuum. Subsequently, the excess of pyridine was washed three times with a 5% HCl solution in a separatory funnel, and the solvent along with water emulsified during the washing were removed by heating under vacuum in the presence of 5 ml of benzene. The product was identified by the appearance of the ester peak at 1780 cm⁻¹ and the disappearance of the acid chloride peak at 1806 cm⁻¹ in the FT-IR spectrum along with the disappearance of OH peak at 4.7 ppm in the NMR spectrum (entries 9–12 in Table 1).

The fluoroether acid chloride used in examples 1–3 was prepared as follows:

5 mmols of oligomers of hexafluoropropylene functionalized at one end with a carboxilic group (MW=2500, 5000, 7500) and 50 cm³ of 1,3-dimethylcyclohexane along with 25 mmols of thyonyl chloride (2.97 g., 1.82 ml) and 10 mmols of N, N dimethyl formamide (0.73 g., 0.77 ml.) were added in a one neck flask equipped with a dry-ice condenser. The reaction mixture was heated at the reflux of thyonyl chloride (t=82° C.) for six hours under a blanket of nitrogen. After reaction, the two phase system was separated in a separator funnel and the solvent was removed under vacuum at 75–80° C. The product was characterized by the disappearance of the carboxilic group peak at 1775 cm⁻¹ and the appearance of the acid chloride peak at 1805 cm⁻¹ in the FT-IR spectrum.

EXAMPLE 4

The following example provides experimental details for a typical hydrogenation process of functionalized anthraquinone prepared as in Example 1–3.

Figure 8:
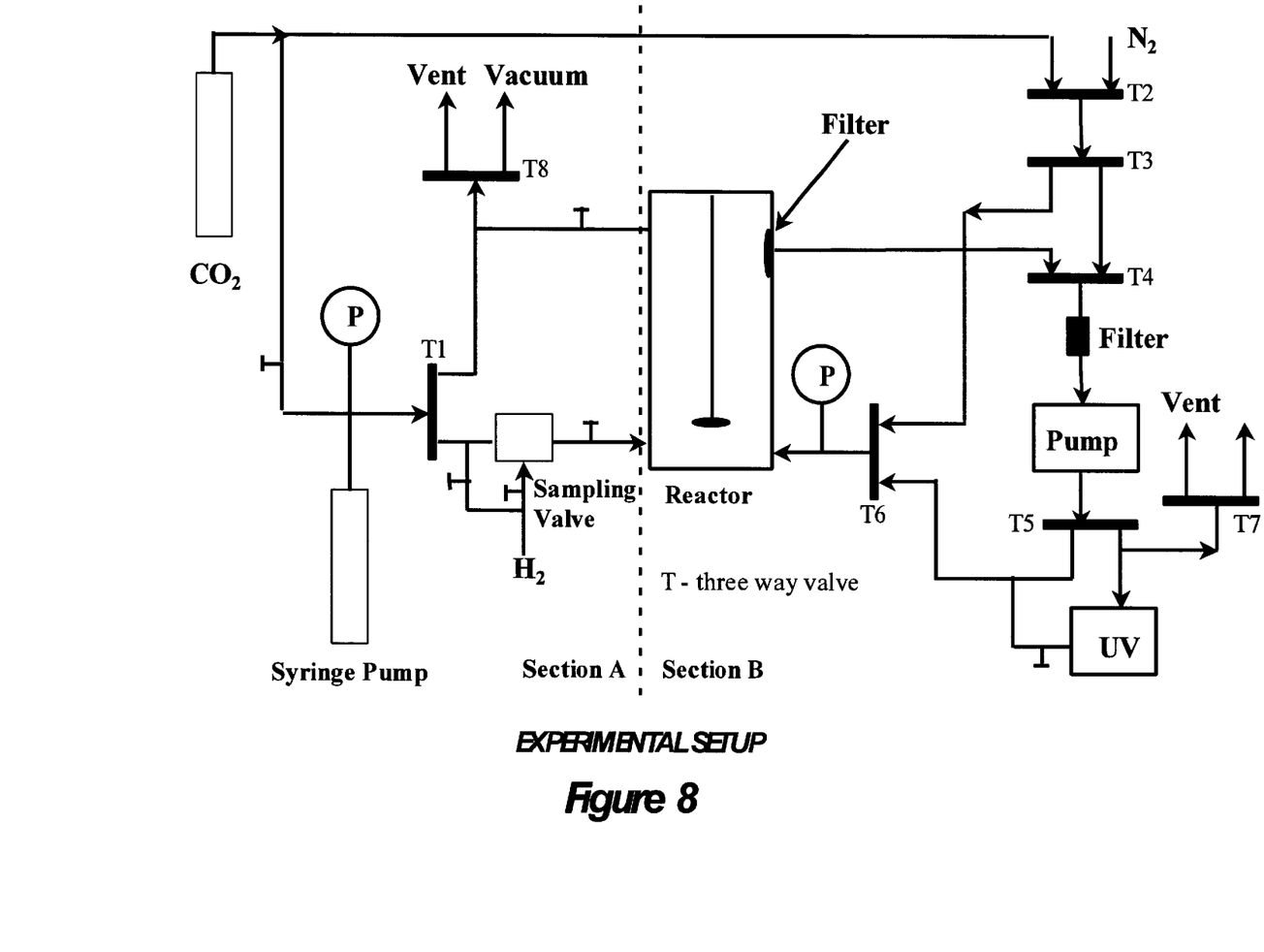
FIG. 8 illustrates one embodiment of a reactor system of the present invention.

Hydrogenation experiments in liquid $CO_2$ were performed using apparatus shown in FIG. 8. The experimental setup consisted of two independent sections. An $H_2$—$CO_2$ mixture was prepared in section A consisting of a syringe pump (High Pressure Equipment) and a sample injection valve (Rheodyne) both connected to a vacuum and venting line. $H_2$—$CO_2$ mixture was prepared in the syringe pump for the experiments requiring a large amount of $H_2$ while the precise amounts of $H_2$ were injected in the reactor through the sample injection valve. The amount of $H_2$ injected in the syringe pump was calculated using a virial equation of state at the pressure indicated by the regulator mounted on the $H_2$ tank. The hydrogenation process was carried in section B consisting of a 35 cm³ stainless steel reactor vessel produced at University of Pittsburgh, and equipped with a mechanical stirrer (modified Parr stirring unit). An internal filter corresponding to the output recirculating port was mounted on the lateral wall of the reactor vessel to prevent entrainment of the catalyst particles in the system.

Figure 6:
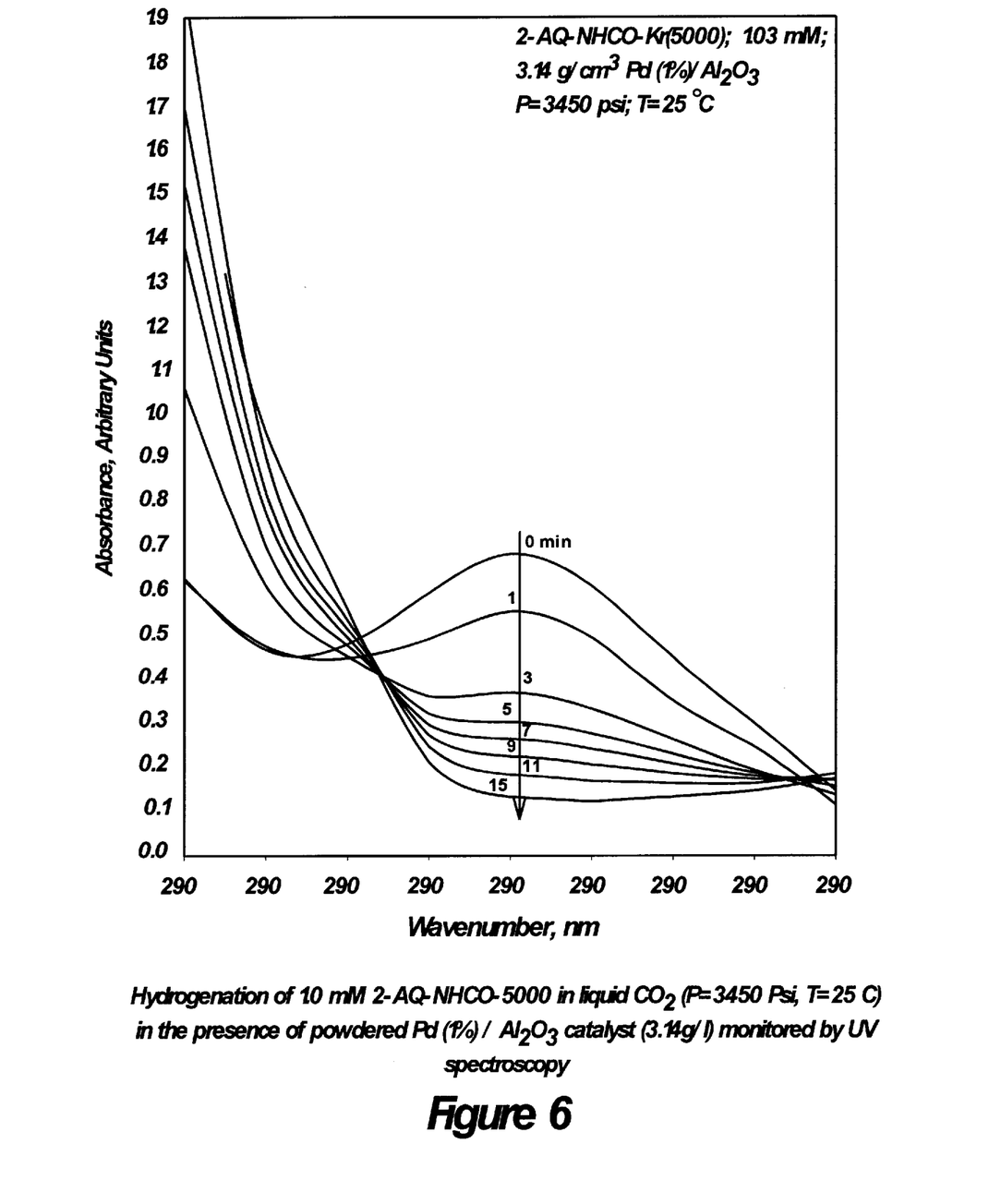
FIG. 6 illustrates the hydrogenation of an analog of anthraquinone as monitored by UV spectroscopy.

In a regular run, the reactor was loaded with one of the FAQ's prepared as described in Example 1–3 and with Pd/Al₂O₃ catalyst. Subsequently, both sections of the system were thoroughly vacuumed at 1–2 mm Hg for 15 minutes to remove any trace of oxygen that might react with H₂FAQ. After the syringe pump in section A was filled with H₂, both sections A and B were pressurized at a pressure of 900–1000 psi bellow the target or operating pressure using a combination of a Haskell gas booster and an Eldex piston pump and supercritical grade carbon dioxide (Praxair). The magnetic stirrer was started in the reactor and the mixture was stirred for 10 minutes to allow enough time for FAQ to dissolve. Meanwhile, the UV adsorption of pure $CO_2$ was measured to be used as reference for the UV measurements of FAQ. After equilibration, the high pressure gear pump (Micropump) was turned on and valve T4 (left) was open to start the circulation of fluid through the UV spectrometer. After stabilization of the UV spectrometer, the initial spectrum of FAQ was recorded in a range between 290–370 nm. Subsequently, the $CO_2$—$H_2$ mixture was injected, and the hydrogenation reaction at room temperature was followed in time by the disappearance of the peak at 320 nm (functionalized esters) or 330 nm (functionalized amides) (FIG. 6). After the reaction was completed, the high pressure reactor was slowly depressurized, and then $H_2$FAQ was exposed to air to produce $H_2O_2$ and regenerate the initial FAQ. Residual FAQ in the vessel was washed with 1,1,2-tricholorotrifluoroethane and the solution was analyzed by IR and NMR.

EXAMPLE 5

Following the procedure of example 4, a functionalized anthraquinone (2-AQ-NHCO-2500) made as per example 1 was used to produce $H_2O_2$. The hydrogenation vessel was charged with 0.055 g FAQ (0.02 mmole; 0.57 mM) and different amounts of 1% Pd/$Al_2O_3$ catalyst, 20–40 mesh. Molar ratio $H_2$:FAQ was 10:1, the operating pressure and temperature were 3450 Psi and 25° C. respectively. The catalyst loading was varied in the range of 2.57–4.28 g/l. Assuming first order reaction with respect to FAQ, the effective rate constant in the hydrogenation process was 0.49 $cm^3$/(g s).

EXAMPLE 6

1% Pd/$Al_2O_3$ catalyst, 40–60 mesh was used in the hydrogenation process as in example 5. Catalyst loading was varied in the range of 2.0–3.42 g/l. Assuming first order reaction with respect to FAQ, the effective rate constant in the hydrogenation process was 0.75 $cm^3$/(g s).

EXAMPLE 7

1% Pd/$Al_2O_3$ catalyst, 60–80 mesh was used in the hydrogenation process as in example 5. Catalyst loading was varied in the range of 1.14–1.71 g/l. Assuming first order reaction with respect to FAQ, the effective rate constant in the hydrogenation process was 1.51 $cm^3$/(g s).

EXAMPLE 8

1% Pd/$Al_2O_3$ powdered catalyst (Aldrich) was used in the hydrogenation process as in example 5. Catalyst loading was varied in the range of 1.14–1.71 g/l. Assuming first order reaction with respect to FAQ, the effective rate constant in the hydrogenation process was 1.81 $cm^3$/(g s).

EXAMPLE 9

Following the procedure of Example 4, a functionalized anthraquinone (2-AQ-NHCO-5000) made as per Example 1 was used to produce $H_2O_2$. The hydrogenation vessel was charged with 0.105 g FAQ (0.02 mmole; 0.57 mM) and different amounts of 1% Pd/$Al_2O_3$ catalyst, 20–40 mesh. Molar ratio of $H_2$:FAQ was 10:1, and the operating pressure and temperature were 3450 Psi and 25° C., respectively. Catalyst loading was varied in the range of 3.71–7.14 g/l. Assuming first order reaction with respect to FAQ, the effective rate constant in the hydrogenation process was 0.30 $cm^3$/(g S).

EXAMPLE 10

1% Pd/$Al_2O_3$ catalyst, 40–60 mesh was used in the hydrogenation process as in example 9. Catalyst loading was varied in the range of 2.57–4.57 g/l. Assuming first order reaction with respect to FAQ, the effective rate constant was 0.45 $cm^3$/(g s).

EXAMPLE 11

1% Pd/$Al_2O_3$ catalyst, 60–80 mesh was used in the hydrogenation process as in example 9. Catalyst loading was varied in the range of 1.56–2.52 g/l. Assuming first order reaction with respect to FAQ, the effective rate constant in the hydrogenation process was 0.85 $cm^3$/(g s).

EXAMPLE 12

1% Pd/$Al_2O_3$ powdered catalyst was used in the hydrogenation process as in example 9. Catalyst loading was varied in the range of 1.14–2.18 g/l. Assuming first order reaction with respect to FAQ, the effective rate constant in the hydrogenation process was 1.83 $cm^3$/(g s).

EXAMPLE 13

Following the procedure of Example 4, a functionalized anthraquinone (2-AQ-NHCO-7500) made as per Example 1 was used to produce $H_2O_2$. The hydrogenation vessel was charged with 0.155 g FAQ (0.02 mmole; 0.57 mM) and different amounts of 1% Pd/$Al_2O_3$ catalyst, 20–40 mesh. Molar ratio of $H_2$:FAQ was 10:1, and the operating pressure and temperature were 3450 Psi and 25° C., respectively. Catalyst loading was varied in the range of 2.52–5.86 g/l. Assuming first order reaction with respect to FAQ, the effective rate constant in the hydrogenation process was 0.22 $cm^3$/(g s).

EXAMPLE 14

1% Pd/$Al_2O_3$ catalyst, 40–60 mesh was used in the hydrogenation process as in example 13. Catalyst loading was varied in the range of 1.9–3.85 g/l. Assuming first order reaction with respect to FAQ, the effective rate constant was 0.32 $cm^3$/(g s).

EXAMPLE 15

1% Pd/$Al_2O_3$ catalyst, 60–80 mesh was used in the hydrogenation process as in example 13. Catalyst loading was varied in the range of 1.54–2.85 g/l. Assuming first order reaction with respect to FAQ, the effective rate constant in the hydrogenation process was 0.72 $cm^3$/(g s).

EXAMPLE 16

1% Pd/$Al_2O_3$ powdered catalyst was used in the hydrogenation process as in example 13. Catalyst loading was varied in the range of 1.54–2.85 g/l. Assuming first order reaction with respect to FAQ, the effective rate constant in the hydrogenation process was 1.11 $cm^3$/(g s).

EXAMPLE 17

Following the procedure of Example 4, a functionalized anthraquinone (2-AQ-$CH_2$OCO-2500) made as per Example 3 was used to produce $H_2O_2$. The hydrogenation vessel was charged with 0.055 g FAQ (0.02 mmole; 0.57 mM) and different amounts of 1% Pd/$Al_2O_3$ catalyst, 20–40 mesh. Molar ratio of $H_2$:FAQ was 10:1, and the operating pressure and temperature were 3450 Psi and 25° C., respectively. Catalyst loading was varied in the range of 2.0–3.85 g/l. Assuming first order reaction with respect to FAQ, the effective rate constant in the hydrogenation process was 0.814 cm$^3$/(g s).

EXAMPLE 18

1% Pd/Al$_2$O$_3$ catalyst, 40–60 mesh was used in the hydrogenation process as in example 17. Catalyst loading was varied in the range of 1.25–1.99 g/l. Assuming first order reaction with respect to FAQ, the effective rate constant in the hydrogenation process was 1.72 cm$^3$/(g s).

EXAMPLE 19

1% Pd/Al$_2$O$_3$ catalyst, 60–80 mesh was used in the hydrogenation process as in example 17. Catalyst loading was varied in the range of 1.06–1.38 g/l. Assuming first order reaction with respect to FAQ, the effective rate constant in the hydrogenation process was 3.38 cm$^3$/(g s).

EXAMPLE 20

1% Pd/Al$_2$O$_3$ powdered catalyst was used in the hydrogenation process as in example 17. Catalyst loading was varied in the range of 0.47–0.9 g/l. Assuming first order reaction with respect to FAQ, the effective rate constant in the hydrogenation process was 3.58 cm$^3$/(g s).

EXAMPLE 21

Following the procedure of Example 4, a functionalized anthraquinone (2-AQ-CH$_2$OCO-5000) made as per Example 3 was used to produce H$_2$O$_2$. The hydrogenation vessel was charged with 0.105 g FAQ (0.02 mmole; 0.57 mM) and different amounts of 1% Pd/Al$_2$O$_3$ catalyst, 20–40 mesh. Molar ratio of H$_2$:FAQ was 10:1, and the operating pressure and temperature were 3450 Psi and 25° C. respectively. Catalyst loading was varied in the range of 2.1–3.44 g/l. Assuming first order reaction with respect to FAQ, the effective rate constant in the hydrogenation process was 0.397 cm$^3$/(g s).

EXAMPLE 22

1% Pd/Al$_2$O$_3$ catalyst, 40–60 mesh was used in the hydrogenation process as in example 21. Catalyst loading was varied in the range of 1.66–3.17 g/l. Assuming first order reaction with respect to FAQ, the effective rate constant in the hydrogenation process was 1.02 cm$^3$/(g s).

EXAMPLE 23

1% Pd/Al$_2$O$_3$ catalyst, 60–80 mesh was used in the hydrogenation process as in example 21. Catalyst loading was varied in the range of 1.18–1.74 g/l. Assuming first order reaction with respect to FAQ, the effective rate constant in the hydrogenation process was 1.41 cm$^3$/(g s).

EXAMPLE 24

1% Pd/Al$_2$O$_3$ powdered catalyst, was used in the hydrogenation process as in example 21. Catalyst loading was varied in the range of 1.02–1.85 g/l. Assuming first order reaction with respect to FAQ, the effective rate constant in the hydrogenation process was 2.02 cm$^3$/(g s).

TABLE 1

Structural Characterization of Functionalized AQ

| Entry | AQ | Kr COCl (MW) | Product | IR | NMR |
|---|---|---|---|---|---|
| 1 | 2-NH$_2$-AQ | 2500 | 2-(2500-NHCO)-AQ | 1539, 1589, 1680 1737, 3321 | 7.25, 8.09, 10.15 |
| 2 | 2-NH$_2$-AQ | 5000 | 2-(5000-CONH)-AQ | 1538, 1589, 1675 1738, 3325 | 7.29, 8.08, 10.21 |
| 3 | 2-NH$_2$-AQ | 7500 | 2-(7500-CONH)-AQ | 1540, 1593, 1675 1738, 3321 | 7.32, 8.15, 10.05 |
| 4 | 1-NH$_2$-AQ | 5000 | 1-(5000-CONH)-AQ | 1419, 1523, 1587, 1677, 1744, 3105 | 8.15–8.30, 9.09 |
| 5 | 1-N(Me)-AQ | 5000 | 1-(5000-CON(Me))-AQ | 1425, 1592, 1675 1740, 3040, 3068 | 2.09, 7.28 8.26, 8.44 |
| 6 | 1,2-NH$_2$-AQ | 2500 | 1,2-Twin(2500)-AQ | 1532, 1599, 1677, 1724, 1739 | 8.11, 9.16, 10.00 |
| 7 | 1,4-NH$_2$-AQ | 2500 | 1,4-Twin(2500)-AQ | 1518, 1597, 1653, 1749 | 7.23, 8.32, 9.16 |
| 8 | 2,6-NH$_2$-AQ | 2500 | 2.6-Twin(2500)-AQ | 1583, 1594, 1678, 1722, 3320 | 8–8.30, 10.33 |
| 9 | 2-(CH$_2$OH)-AQ | 700[a] | 2-(700-COO-CH$_2$)-AQ[(1)] | 1440, 1592, 1674, 1778, 3045, 3065 3321 | 2.08, 5.45, 8.24 |
| 10 | 2-(CH$_2$OH)-AQ | 2500 | 2-(2500-COO-CH$_2$)-AQ | 1441, 1593, 1674, 1779, 3046, 3065 3322 | 2.11, 5.46, 8.23 |
| 11 | 2-(CH$_2$OH)-AQ | 5000 | 2-(5000-COO-CH$_2$)-AQ | 1443, 1593, 1675 1780, 3046, 3066 3323 | 2.09, 5.45, 8.25 |
| 12 | 2-(CH$_2$OH)-AQ | 7500 | 2-(7500-COO-CH$_2$)-AQ | 1441, 1593, 1675 1779, 3046, 3066 3323 | 2.04 5.43 8.29 |

[(1)]Prepared as in Example 3 from perfluoro-2,5,8-trimethyl-3,6,9-trioxadodecanoyl fluoride and 2-(hydroxymethyl)-anthraquinone.

TABLE 2

Mass transfer and kinetic parameters

| MM | $k_c^{(1)}$ cm³/(g s) | | $D_e^{(1)}$ cm²/s 10⁵ | | $\eta^{(2)}$ | |
|---|---|---|---|---|---|---|
| | Amide | Ester | Amide | Ester | Amide | Ester |
| 2500 | 2.12 | 3.83 | 9.91 | 12.5 | 0.85 | 0.92 |
| 5000 | 2.12 | 3.83 | 4.6 | 4.25 | 0.85 | 0.903 |
| 7500 | 2.12 | | 1.81 | | 0.4 | |
| 2-EtAQ | 0.47[(3)] | | | | | |

[(1)]Value determined from the regression s vs $d_p$; where s is the slope of the linear dependence $1/k_{eff}$ vs $1/w$ ($d_p$ - particle size; w - catalyst loading);
[(2)]$\eta = k_c/k_{powd}$ ($k_{powd}$ - effective rate constant determined experimentally for the powdered catalyst)
[(3)]Value obtained by extrapolation of the data from Santacesaria, E.; Di Serio, M.; Velotti, R.; Leone, U. Ind. Eng. Chem. Res., 1994, 33, 277.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A chemical compound having the formula:

wherein $R^1$, $R^2$, $R^3$, $R^4$, $R^5$, $R^6$, $R^7$, and $R^8$ are independently, the same or different, selected from H, $R^C$, or $R^S R^C$, wherein $R^S$ is a spacer group and $R^C$ is $CO_2$-philic group selected from a fluoroalkyl group, a fluoroether group, a silicone group, an alkylene oxide group, a fluorinated acrylate group, or a phosphazine group, and wherein at least one of $R^1$, $R^2$, $R^3$, $R^4$, $R^5$, $R^6$, $R^7$, and $R^8$ is not H such that the compound is $CO_2$-philic.

2. The chemical of claim 1 wherein the spacer group is an alkyl group, an amino group, an amido group, an alkyl ester group or an ester group.

3. The chemical compound of claim 2 wherein the spacer group is —NHCO—, —N(CH₃)C(O)— or —CH₂OCO—.

4. The chemical compound of claim 1 wherein molecular weight of the fluoroalkyl group, the fluoroether group, the silicone group or the alkylene oxide group is between approximately 50 and approximately 7500.

5. The chemical compound of claim 1 wherein molecular weight of the fluoroalkyl group, the fluoroether group, the silicone group or the alkylene oxide group is between approximately 500 and approximately 5000.

6. The chemical compound of claim 1 wherein molecular weight of the fluoroalkyl group, the fluoroether group, the silicone group or the alkylene oxide group is between approximately 500 and approximately 1500.

7. The chemical compound of claim 1 wherein the fluoroalkyl group has the formula:

wherein g is an integer and the fluoroalkyl group has a molecular weight between approximately 200 and approximately 7500.

8. The chemical compound of claim 1 wherein the fluoroether group has the formula:

wherein each of x, y and z is an integer greater than or equal to 0 and at least one of x, y and z is not equal to 0 and the fluoroether group has a molecular weight between approximately 200 and approximately 7500.

9. The chemical compound of claim 1 wherein the silicone group has the formula:

wherein $R^9$ and $R^{10}$ are, independently, the same or different, selected from H, an alkyl group, a fluoroalkyl group, an aryl group, an alkenyl group, and an alkoxyl group, wherein b is an integer and the silicone group has a molecular weight between approximately 200 and approximately 7500.

10. The chemical compound of claim 9 wherein $R^9$ or $R^{10}$ is a fluoroalkyl group.

11. The chemical compound of claim 1 wherein the alkylene oxide group has the formula:

wherein d is an integer and e is an integer greater than or equal to 0 and the alkylene oxide group has a molecular weight between approximately 200 and approximately 7500.

12. The chemical compound of claim 1 wherein the phosphazine group has the formula:

wherein $R^9$ and $R^{10}$ are, independently, the same or different, selected from H, an alkyl group, a fluoroalkyl group, an aryl group, an alkenyl group, and an alkoxyl group, wherein b is an integer and the silicone group has a molecular weight between approximately 200 and approximately 7500.

13. A chemical compound having the formula:

wherein $R^1$, $R^2$, $R^3$, $R^4$, $R^5$, $R^6$, $R^7$, and $R^8$ are independently, the same or different, selected from H, $R^C$, or $R^SR^C$, wherein $R^S$ is a spacer group and $R^C$ is a $CO_2$-philic group selected from fluoroalkyl group, a fluoroether group, a silicone group, an alkylene oxide group, a fluorinated acrylate group, or a phosphazine group, and wherein at least one of $R^1$, $R^2$, $R^3$, $R^4$, $R^5$, $R^6$, $R^7$, and $R^8$ is not H so that the compound is $CO_2$-philic.

* * * * *